US009161936B2

(12) United States Patent
Martino et al.

(10) Patent No.: US 9,161,936 B2
(45) Date of Patent: *Oct. 20, 2015

(54) LAQUINIMOD FOR TREATMENT OF GABA MEDIATED DISORDERS

(71) Applicants: Gianvito Martino, Bergamo (IT); Diego Centonze, Rome (IT)

(72) Inventors: Gianvito Martino, Bergamo (IT); Diego Centonze, Rome (IT)

(73) Assignee: TEVA PHARMACEUTICAL INDUSTRIES, LTD., Petach-Tikva (IL)

(*) Notice: Subject to any disclaimer, the term of this patent is extended or adjusted under 35 U.S.C. 154(b) by 0 days.

This patent is subject to a terminal disclaimer.

(21) Appl. No.: 13/964,959

(22) Filed: Aug. 12, 2013

(65) Prior Publication Data

US 2014/0045886 A1    Feb. 13, 2014

Related U.S. Application Data

(60) Provisional application No. 61/682,576, filed on Aug. 13, 2012.

(51) Int. Cl.
  *A61K 31/4704* (2006.01)
(52) U.S. Cl.
  CPC .................................. *A61K 31/4704* (2013.01)
(58) Field of Classification Search
  CPC .................................................. A61K 31/4704
  See application file for complete search history.

(56) References Cited

U.S. PATENT DOCUMENTS

| 6,077,851 | A  | 6/2000  | Bjork et al.     |
| 6,121,287 | A  | 9/2000  | Bjork et al.     |
| 6,133,285 | A  | 10/2000 | Bjork et al.     |
| 6,307,050 | B1 | 10/2001 | Kwiatkowski et al. |
| 6,593,343 | B2 | 7/2003  | Bjork et al.     |
| 6,605,616 | B1 | 8/2003  | Bjork et al.     |
| 6,696,407 | B1 | 2/2004  | Longo et al.     |
| 6,875,869 | B2 | 4/2005  | Jansson          |
| 7,485,311 | B2 | 2/2009  | Lue et al.       |
| 7,560,100 | B2 | 7/2009  | Pinchasi et al.  |
| 7,560,557 | B2 | 7/2009  | Jansson          |
| 7,589,208 | B2 | 9/2009  | Jansson et al.   |
| 7,884,208 | B2 | 2/2011  | Frenkel et al.   |
| 7,989,473 | B2 | 8/2011  | Patashnik et al. |
| 8,178,127 | B2 | 5/2012  | Safadi et al.    |
| 8,252,933 | B2 | 8/2012  | Gant et al.      |
| 8,314,124 | B2 | 11/2012 | Jansson et al.   |
| 8,383,645 | B2 | 2/2013  | Patashnik et al. |
| 8,501,766 | B2 | 8/2013  | Kaye et al.      |
| 8,545,885 | B2 | 10/2013 | Safadi et al.    |
| 8,580,819 | B2 | 11/2013 | Piryatinsky et al. |
| 8,598,203 | B2 | 12/2013 | Tarcic et al.    |
| 8,647,646 | B2 | 2/2014  | Frenkel et al.   |
| 8,673,322 | B2 | 3/2014  | Frenkel et al.   |
| 8,809,537 | B2 | 8/2014  | Laxer et al.     |
| 8,889,627 | B2 | 11/2014 | Hallak et al.    |
| 8,889,661 | B2 | 11/2014 | Haviv et al.     |
| 2002/0173520 | A1 | 11/2002 | Bjork et al.     |
| 2005/0192315 | A1 | 9/2005  | Jansson et al.   |
| 2005/0215586 | A1 | 9/2005  | Jansson et al.   |
| 2008/0063607 | A1 | 3/2008  | Tamarkin et al.  |
| 2010/0168099 | A1 | 7/2010  | Falco et al.     |
| 2010/0190771 | A1 | 7/2010  | Claffey et al.   |
| 2010/0322900 | A1 | 12/2010 | Tarcic et al.    |
| 2011/0034508 | A1 | 2/2011  | Hayardeny        |
| 2011/0217295 | A1 | 9/2011  | Haviv et al.     |
| 2011/0251235 | A1 | 10/2011 | Patashnik et al. |
| 2012/0010239 | A1 | 1/2012  | Fristedt         |
| 2012/0142730 | A1 | 6/2012  | Tarcic et al.    |
| 2013/0028866 | A1 | 1/2013  | Gilgun et al.    |
| 2013/0029916 | A1 | 1/2013  | Gilgun et al.    |
| 2013/0184310 | A1 | 7/2013  | Haviv and Tarcic |
| 2013/0203807 | A1 | 8/2013  | Tarcic et al.    |
| 2013/0217724 | A1 | 8/2013  | Ioffe at al      |
| 2013/0259856 | A1 | 10/2013 | Kaye             |
| 2013/0272996 | A1 | 10/2013 | Tarcic et al.    |
| 2013/0303569 | A1 | 11/2013 | Bar-Zohar        |
| 2013/0324574 | A1 | 12/2013 | Kaye et al.      |
| 2013/0345257 | A1 | 12/2013 | Hahn             |
| 2014/0017226 | A1 | 1/2014  | Kaye et al.      |
| 2014/0018386 | A1 | 1/2014  | Sarfati et al.   |
| 2014/0024678 | A1 | 1/2014  | Safadi et al.    |
| 2014/0045887 | A1 | 2/2014  | Martino et al.   |
| 2014/0051723 | A1 | 2/2014  | Piryatinsky et al. |
| 2014/0057883 | A1 | 2/2014  | Tarcic et al.    |
| 2014/0107154 | A1 | 4/2014  | Filippi et al.   |
| 2014/0128430 | A1 | 5/2014  | Frenkel et al.   |

(Continued)

FOREIGN PATENT DOCUMENTS

| EP | 1073639 | 11/2002 |
| EP | 1097139 | 12/2002 |

(Continued)

OTHER PUBLICATIONS

Bruck et al. "Insight into the mechanism of laquinimod action". Journal of the Neurological Sciences 306 (2011) 173-179.*

PCT International Preliminary Report on Patentability issued Feb. 14, 2012 in connection with PCT International Application No. PCT/US2010/02194, filed Aug. 9, 2010.

PCT International Search Report issued Dec. 23, 2013 in connection with PCT International Application No. PCT/US2013/54563, filed Aug. 12, 2013.

PCT International Search Report issued Jan. 2, 2014 in connection with PCT International Application No. PCT/US2013/54561, filed Aug. 12, 2013.

PCT International Search Report issued Oct. 5, 2010 in connection with PCT International Application No. PCT/US2010/02194, filed Aug. 9, 2010.

(Continued)

*Primary Examiner* — Renee Claytor

(74) *Attorney, Agent, or Firm* — John P. White; Gary J. Gershik; Cooper & Dunham LLP

(57) ABSTRACT

This invention provides a method of treating a subject suffering from a GABA related disorder comprising periodically administering to the subject an effective amount of laquinimod or pharmaceutically acceptable salt thereof in an amount effective to treat the subject.

20 Claims, 7 Drawing Sheets

(56) References Cited

U.S. PATENT DOCUMENTS

2014/0171647 A1    6/2014    Frenkel et al.
2014/0271878 A1    9/2014    Frenkel et al.

FOREIGN PATENT DOCUMENTS

| | | |
|---|---|---|
| EP | 1095021 | 9/2003 |
| EP | 1511732 | 12/2006 |
| EP | 1720531 | 4/2011 |
| WO | WO 99/55678 | 11/1999 |
| WO | WO 00/03991 | 1/2000 |
| WO | WO 00/03992 | 1/2000 |
| WO | WO 03/106424 | 12/2003 |
| WO | WO 2005/066126 | 7/2005 |
| WO | WO 2005/074899 | 8/2005 |
| WO | WO 2006/076681 | 7/2006 |
| WO | WO 2008/079270 | 7/2008 |
| WO | WO 2010/057006 | 5/2010 |
| WO | WO 2012/062925 | 5/2012 |
| WO | WO 2014/152009 | 3/2014 |

OTHER PUBLICATIONS

Written Opinion of the International Searching Authority issued Dec. 23, 2013 in connection with PCT International Application No, PCT/US2013/54563 filed Aug. 12, 2013.

Written Opinion of the International Searching Authority issued Jan. 2, 2014 in connection with PCT International Application No. PCT/US2013/54561 filed Aug. 12, 2013.

Written Opinion of the International Searching Authority issued Jan. 2, 2014 in connection with PCT International Application No. PCT/US2013/54563 filed Aug. 12, 2013.

Written Opinion of the International Searching Authority issued Oct. 5, 2010 in connection with PCT International Application No. PCT/US2010/02194 filed Aug. 9, 2010.

Acheson et al. (1995) "A BDNF autocrine loop in adult sensory neurons prevents cell death". Nature, 374(6521):450-453.

Alonso et al. (2005) "Endogenous BDNF is required for long-term memory formation in the rat parietal cortex" Learning & Memory, 12(5):504-510.

Caffe et al. (2001) "A combination of CNTF and BDNF rescues rd photoreceptors but changes rod differentiation in the presence of RPE in retinal explants" Investigative Ophthalmology & Visual Science, 42:275-82.

Chen et al. (2009) "Kynurenine Pathway Metabolites in Humans: Disease and Healthy States" Int J Tryptophan Res. 2009; 2:11-19.

Chen et al. (2009) "Recent Advances in the Treatment of Amyotrophic Lateral Sclerosis . . . " Central Nervous System Agents in Medicinal Chemistry (9):31-39.

Chen et al. (2012) "The Kynurenine pathway", Chapter 15, Amyotrophic Lateral Sclerosis, book edited by Martin H. Maurer, ISBN 978-953-307-806-9.

Chesselet (2003) "Dopamine and Parkinson's disease: is the killer in the house?" Molecular Psychiatry, 8(4):369-370.

Howells et al. (2000) "Reduced BDNF mRNA expression in the Parkinson's disease substantia nigra". Experimental Neurology, 166(1):127-135.

Hu and Russek (2008) "BDNF and the diseased nervous system: a delicate balance between 3 adaptive and pathological processes of gene regulation" J. of Neurochemistry, 105:1-17.

Huang and Reichardt (2001) "Neurotrophins: roles in neuronal development and function", Annu. Rev. Neurosci. 24:677-736.

Mintz et al. (20040 "Ocular Manifestations of Inflammatory Bowel Disease", Inflamm. Bowel Dis. 10(2):135-9.

Reagan-Shaw et al. (2007) "Dose translation from animal to huan studies revisited", FASEB J 22:659-661.

Sen et al. (2008) "Serum brain-derived neurotrophic factor, depression, and antidepressant medications: meta-analyses and implication", Biol. Psychiatry, 64(6):527-32.

Snider et al. (1989) "Neurotrophic molecules", Ann. Neurol 26(4):489-506.

Tramontina et al. (2009) "Brain-derived neurotrophic factor serum levels before and after treatment for acute mania", Neuroscience Letters, 452(2):111-3.

Tuvesson et al. (2005) "Cytochrome P450 3A4 Is the Major Enzyme Responsible for the Metabolism of Laquinimod, A Novel Immunomodulator", Drug Metabolism and Disposition, 33(6):866-72.

\* cited by examiner

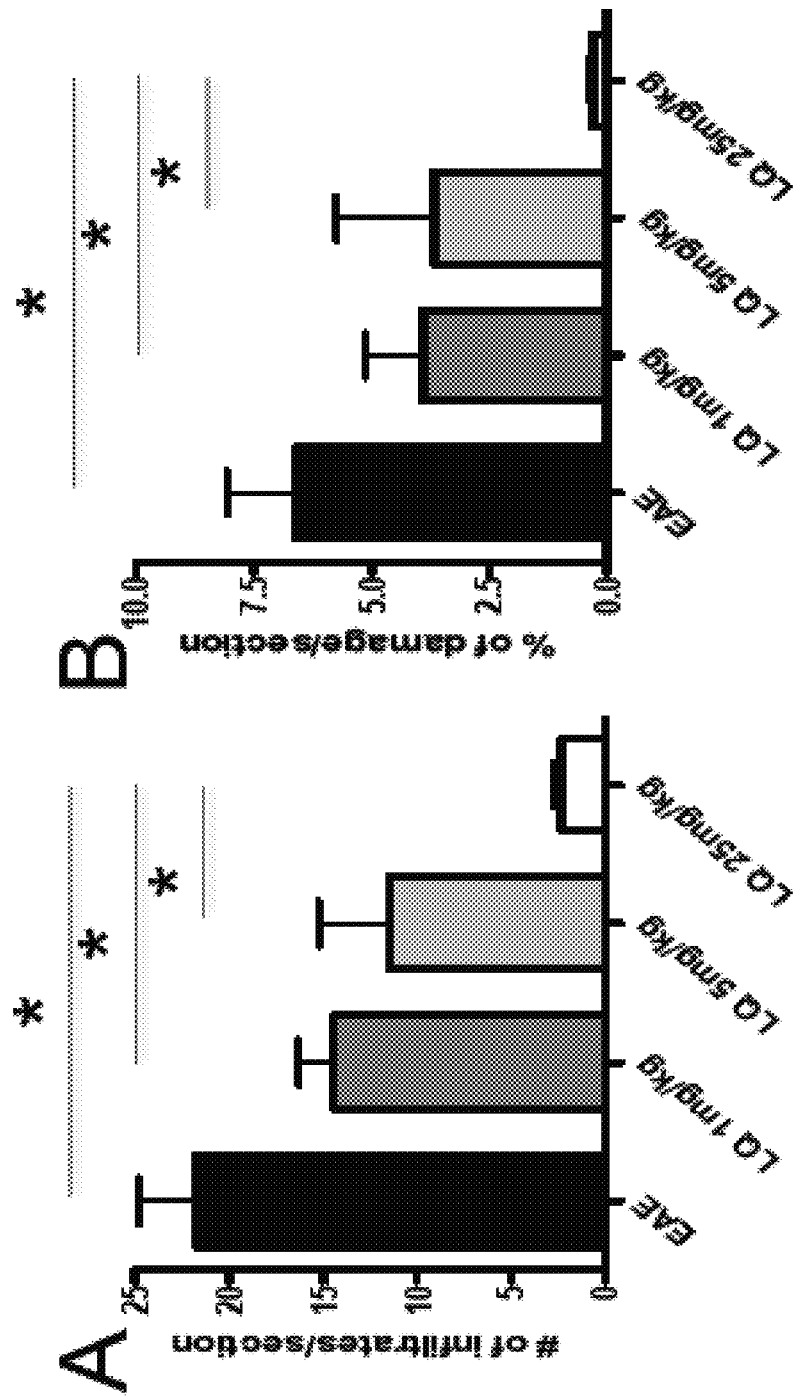
FIGURE 2 (A-B)

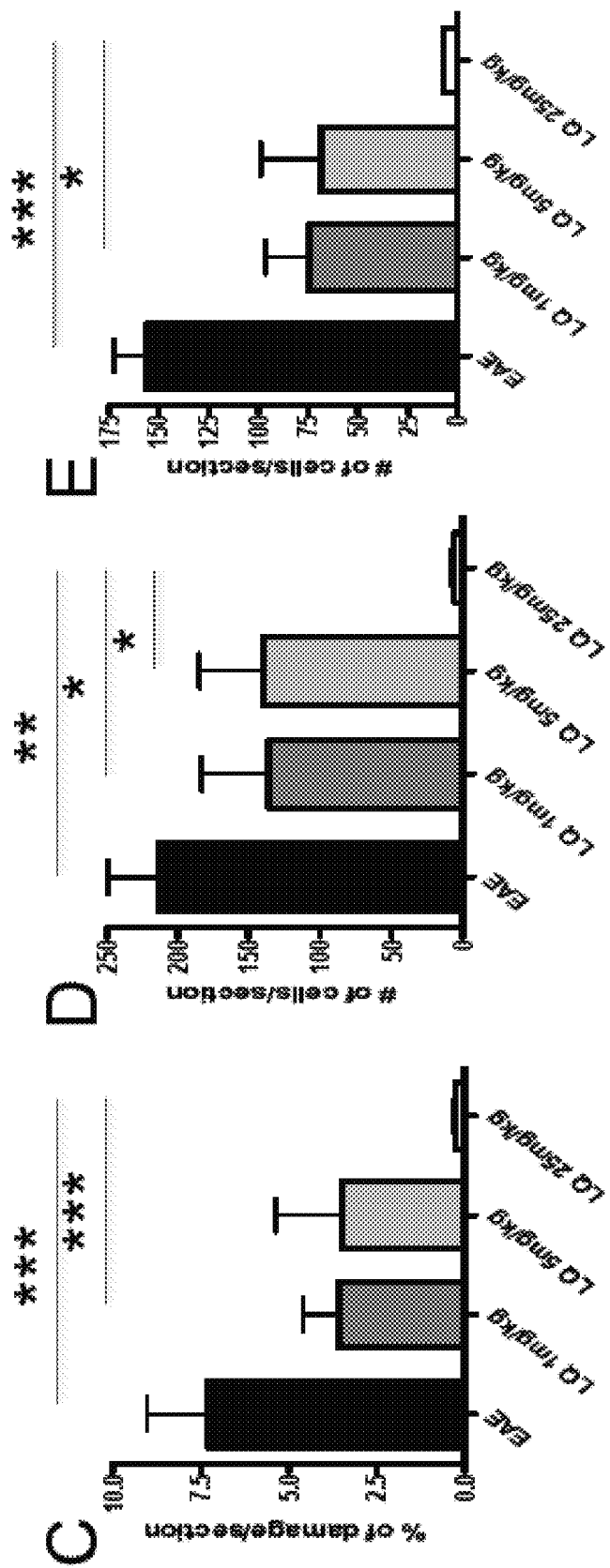
FIGURE 2 (C-E)

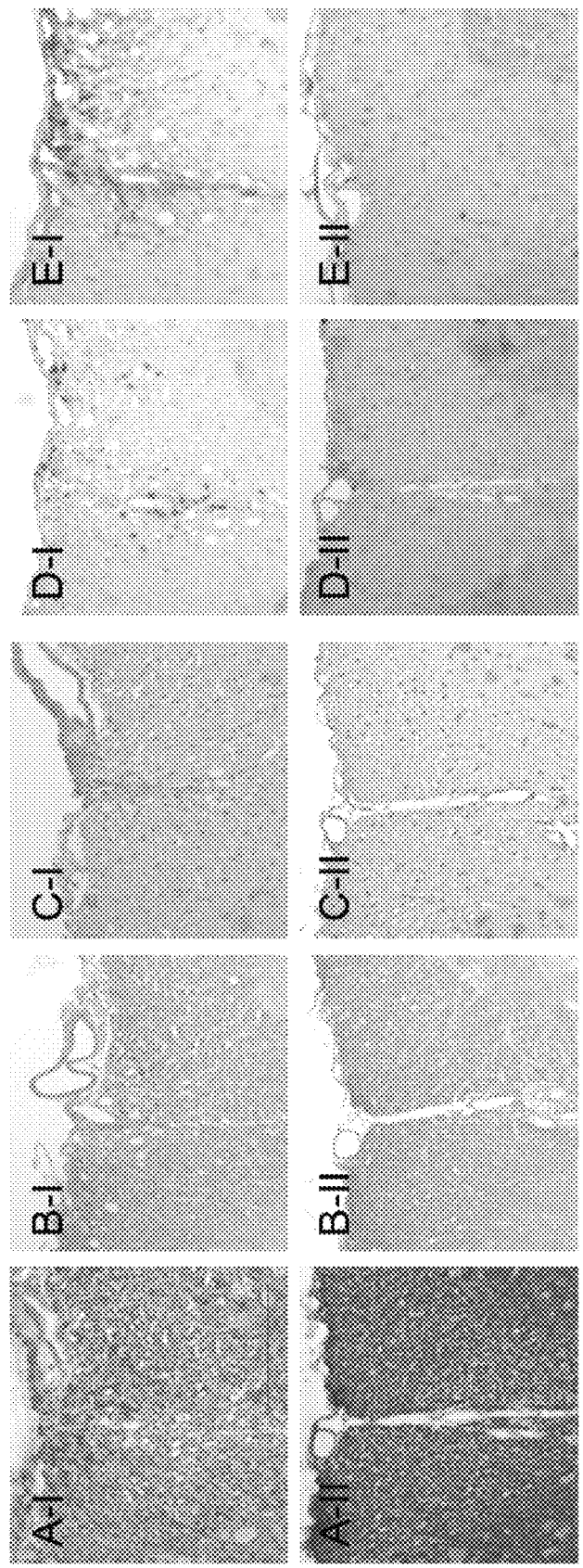
FIGURE 2 (A-I-E-I, AII-EII)

FIGURE 3
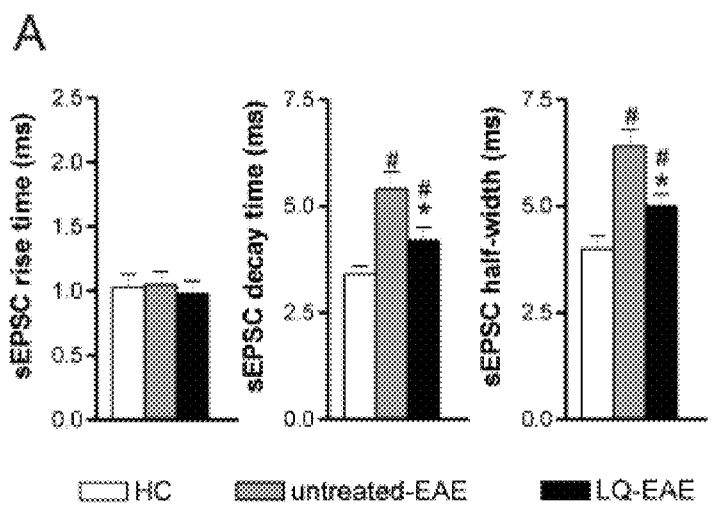
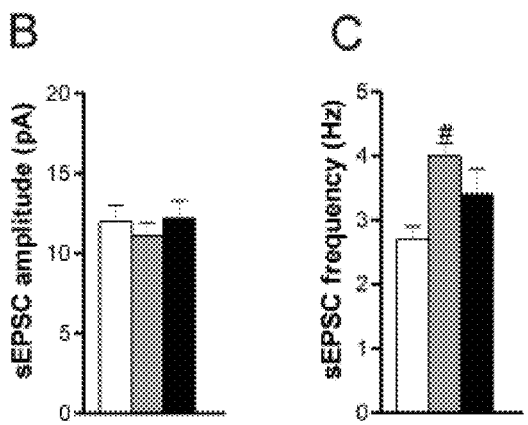
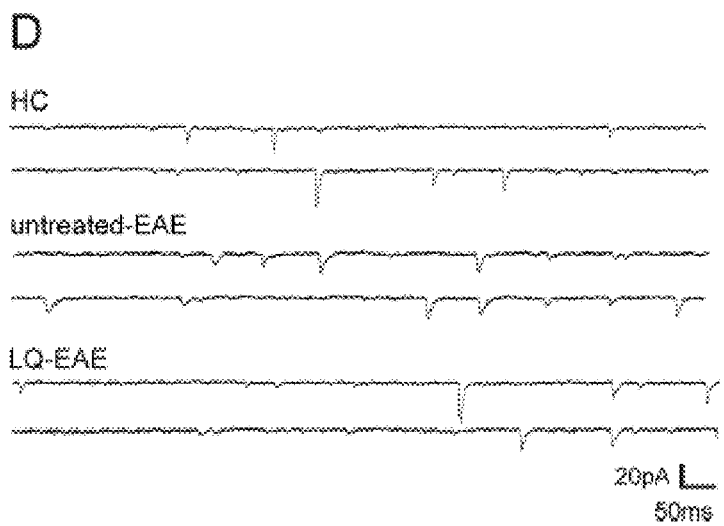

LAQUINIMOD FOR TREATMENT OF GABA MEDIATED DISORDERS

This application claims benefit of U.S. Provisional Application No. 61/682,576, filed Aug. 13, 2012, the entire content of which is hereby incorporated by reference herein.

Throughout this application various publications are referenced. The disclosures of these publications in their entireties are hereby incorporated by reference into this application in order to more fully describe the state of the art to which this invention pertains.

BACKGROUND

Gamma-aminobutyric acid (GABA) is the main inhibitory neurotransmitter in the central nervous system (CNS). GABA is produced by the conversion of glutamic acid to GABA by glutamic acid decarboxylase and is released by GABAergic neurons in the CNS. (Wong et al., 2003). Upon release, GABA binds to neuronal transmembrane GABA receptors. The $GABA_A$ receptor is a chloride ion channel which is regulated by GABA binding and is the major site for the inhibitory activities of GABA. Specifically, the binding of GABA to the $GABA_A$ receptor opens the chloride ion channel. In mature neurons, the opening of the chloride channel results in a decrease of the transmembrane potential and thereby inhibits neuronal excitation. (Olsen, 2002). Through this mechanism, GABA is known to regulate the activity of central noradrenergic, serotonergic, dopaminergic and acetylcholinergic neurons. (Wenk et al., 1991). As described below, GABAergic dysfunction has been linked to several disorders.

Schizophrenia is a mental disorder characterized by a loss of contact with reality, hallucinations, delusions, abnormal thinking, flattened affect, diminished motivation, and disturbed work and social functioning. (Merck Manual, Seventh Ed.). It has been hypothesized that decreased GABAergic transmission causes rearrangement, and possibly enlargement of sensory, memory and 'cognitive' fields, which may lead to overinclusive and disorganized thought processes associated with schizophrenia. Post-mortem studies of schizophrenic subjects have shown that defects of GABAergic neurotransmission are implicated in schizophrenia and bipolar disorder. (Bernes & Berretta, 2001).

Due to the inhibitory function of GABA in the CNS, disruptions in GABAeric function has been implicated in epilepsy (seizures), spasticity, stiff-person syndrome (SPS), premenstrual dysphoric disorder, drug addiction, anxiety disorders, and schizophrenia (Wong et al., 2003), and fertility disorders (Sullivan & Moenter, 2003).

Deficits in $GABA_A$ receptors have been linked to anxiety, epilepsy, and insomnia. (Möhler, 2006).

GABA levels were found to be lower in the cerebrospinal fluid of patients with spinocerebellar degeneration, neuro-Behçet's syndrome and Parkinson's disease. (Kuroda et al., 1982).

A loss of CB1 receptor control of GABA-mediated synaptic currents has been shown in the mouse model of attention-deficit/hyperactivity disorder. Specifically, in the mouse model of ADHD obtained by triple point mutation in the dopamine transporter (DAT) gene, sensitivity of CB1 receptors controlling GABA-mediated synaptic currents in the striatum was completely lost. (Castelli et al., 2011).

SUMMARY OF THE INVENTION

Disclosed herein is that laquinimod treats GABA-related disorders.

Laquinimod is a novel synthetic compound with high oral bioavailability, which has been suggested as an oral formulation for Relapsing Remitting Multiple Sclerosis (RRMS).

The relationship between laquinimod and GABAergic function has not been reported. U.S. Pat. Nos. 7,989,473 and 8,178,127 and disclose stable preparations of N-ethyl-N-phenyl-1,2-dihydro-4-hydroxy-5-chloro-1-methyl-2-oxoquinoline-3-carboxamide (CAS Number 248281-84-7), also known as laquinimod. Laquinimod has been shown in U.S. Pat. No. 6,077,851 to be effective in the acute experimental autoimmune encephalomyelitis (aEAE) model. U.S. Pat. No. 6,077,851 discloses the synthesis of laquinimod and the preparation of its sodium salt. U.S. Pat. No. 6,875,869 discloses an additional synthesis process of laquinimod.

This invention provides a method of treating a subject suffering from a GABA related disorder comprising periodically administering to the subject an effective amount of laquinimod or pharmaceutically acceptable salt thereof in an amount effective to treat the subject.

This invention also provides a method of decreasing the duration or frequency of spontaneous glutamate-mediated excitatory postsynaptic currents (sEPSCs) in a human subject comprising periodically administering to the subject an effective amount of laquinimod or pharmaceutically acceptable salt thereof.

This invention also provides a method of increasing the duration or frequency of $GABA_A$-mediated inhibitory postsynaptic currents (sIPSCs) in a human subject comprising periodically administering to the subject an effective amount of laquinimod or pharmaceutically acceptable salt thereof.

This invention also provides a method of preventing the alteration of $GABA_A$-mediated inhibitory postsynaptic currents (sIPSCs) in a human subject comprising periodically administering to the subject an effective amount of laquinimod or pharmaceutically acceptable salt thereof.

This invention also provides a use of laquinimod in the manufacture of a medicament for treating a human subject suffering from a GABA related disorder.

This invention also provides a use of laquinimod in the manufacture of a medicament for decreasing the duration or frequency of spontaneous glutamate-mediated excitatory postsynaptic currents (sEPSCs) in a human subject.

This invention also provides a use of laquinimod in the manufacture of a medicament for increasing the duration or frequency of $GABA_A$-mediated inhibitory postsynaptic currents (sIPSCs) in a human subject.

This invention also provides a use of laquinimod in the manufacture of a medicament for preventing the alteration of $GABA_A$-mediated inhibitory postsynaptic currents (sIPSCs) in a human subject.

This invention also provides a pharmaceutical composition comprising an amount of laquinimod effective for use in treating a human subject suffering from a GABA related disorder.

This invention also provides a pharmaceutical composition comprising an amount of laquinimod effective for use in decreasing the duration or frequency of spontaneous glutamate-mediated excitatory postsynaptic currents (sEPSCs) in a human subject.

This invention also provides a pharmaceutical composition comprising an amount of laquinimod effective for use in increasing the duration or frequency of $GABA_A$-mediated inhibitory postsynaptic currents (sIPSCs) in a human subject.

This invention also provides a pharmaceutical composition comprising an amount of laquinimod effective for use in preventing the alteration of $GABA_A$-mediated inhibitory postsynaptic currents (sIPSCs) in a human subject.

BRIEF DESCRIPTION OF THE FIGURES

FIG. 2: Subcutaneous treatment with LQ significantly reduces myelin loss, axonal damage and inflammation. A significant reduction of CD3+ T cells and IB4+ macrophages was observed in LQ-EAE mice vs. untreated-EAE mice. An average of 10-15 spinal cord sections per mouse and a total of 4 mice per treatment group were used. (A) Axonal damage measured as percentage over the total section area. (B) Demyelination measured as percentage over the total section area. (C) Perivascular infiltrates measured as numbers of infiltrates per section. (D) CD3+ T cells measured as numbers of cells per sections. (E) IB4+ macrophages measured as numbers of cells per sections. X-I and X-II representative picture from untreated EAE mice and 25 mg/kg LQ-EAE mice, respectively. Statistical analysis was performed using unpaired Student T-test. *=$p<0.05$; =$p<0.002$; *=$p<0.0001$. Scale bars: 100 μm.

FIG. 3: Effect of LQ treatment on EAE-induced synaptic alterations of striatal glutamatergic transmission. (A) The duration of glutamate-mediated sEPSCs was increased in striatal neurons of untreated EAE mice, due to an increase of half-width and decay time. LQ treatment failed to prevent the alteration of sEPSC shape but significantly reduced it. (B) sEPSC amplitude was comparable in untreated-EAE, LQ-EAE and wild type control mice (HC). (C) The frequency of glutamatergic sEPSCs was up-regulated in EAE mice, and reduced, although not normalized, by LQ treatment. (D) The electrophysiological traces are examples of sEPSCs recorded from striatal neurons of HC, untreated (sham) EAE and 25 mg/kg LQ-EAE mice. Statistical analysis was performed using ANOVA followed by Tukey HSD Test. *$p<0.05$ compared to untreated-EAE group; # means $p<0.05$ compared to HC.

DETAILED DESCRIPTION OF THE INVENTION

Figure 1:
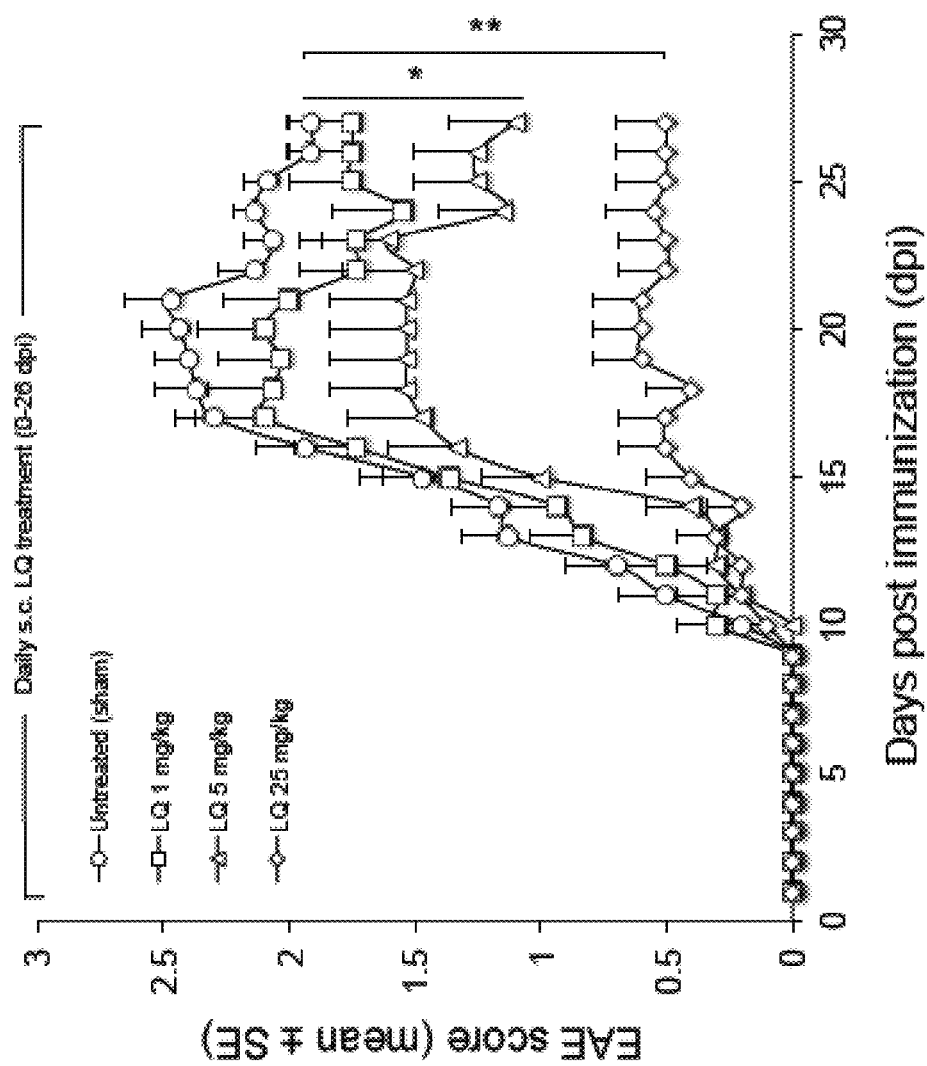
FIG. 1: Preventive treatment (0-26 dpi) with daily s.c. administration of LQ (1-25 mg/kg) significantly suppresses EAE in a dose-dependent manner. A reduction in the incidence of the disease and a delayed disease onset was observed (15 mice per treatment group). Statistical analysis was performed using unpaired Student T-test. *=$p<0.05$; **=$p<0.0001$.

This invention provides a method of treating a subject suffering from a GABA related disorder comprising periodically administering to the subject an effective amount of laquinimod or pharmaceutically acceptable salt thereof in an amount effective to treat the subject.

In one embodiment, the subject is human. In another embodiment, the GABA related disorder is schizophrenia, epilepsy (seizures), spasticity, stiff-person syndrome (SPS), premenstrual dysphoric disorder, drug addiction, or fertility disorder. In another embodiment, the GABA related disorder is insomnia, spinocerebellar degeneration, or neuro-Behçet's syndrome.

This invention also provides a method of decreasing the duration or frequency of spontaneous glutamate-mediated excitatory postsynaptic currents (sEPSCs) in a human subject comprising periodically administering to the subject an effective amount of laquinimod or pharmaceutically acceptable salt thereof.

This invention also provides a method of increasing the duration or frequency of $GABA_A$-mediated inhibitory postsynaptic currents (sIPSCs) in a human subject comprising periodically administering to the subject an effective amount of laquinimod or pharmaceutically acceptable salt thereof.

This invention also provides a method of preventing the alteration of $GABA_A$-mediated inhibitory postsynaptic currents (sIPSCs) in a human subject comprising periodically administering to the subject an effective amount of laquinimod or pharmaceutically acceptable salt thereof.

In one embodiment, the GABA concentration in the central nervous system of the subject is increased.

In one embodiment, the laquinimod is administered via oral administration. In another embodiment, the laquinimod is administered daily. In another embodiment, the laquinimod is administered more often than once daily. In another embodiment, the laquinimod is administered less often than once daily.

In one embodiment, the amount of laquinimod in the composition is less than 0.6 mg. In another embodiment, the amount of laquinimod in the composition is 0.1-40.0 mg. In another embodiment, the amount of laquinimod in the composition is 0.1-2.5 mg. In another embodiment, the amount of laquinimod in the composition is 0.25-2.0 mg. In another embodiment, the amount of laquinimod in the composition is 0.5-1.2 mg. In another embodiment, the amount of laquinimod in the composition is 0.25 mg. In another embodiment, the amount of laquinimod in the composition is 0.3 mg. In another embodiment, the amount of laquinimod in the composition is 0.5 mg. In another embodiment, the amount of laquinimod in the composition is 0.6 mg. In another embodiment, the amount of laquinimod in the composition is 1.0 mg. In another embodiment, the amount of laquinimod in the composition is 1.2 mg. In another embodiment, the amount of laquinimod in the composition is 1.5 mg. In another embodiment, the amount of laquinimod in the composition is 2.0 mg.

In one embodiment, the pharmaceutically acceptable salt of laquinimod is laquinimod sodium.

This invention also provides a use of laquinimod in the manufacture of a medicament for treating a human subject suffering from a GABA related disorder.

This invention also provides a use of laquinimod in the manufacture of a medicament for decreasing the duration or frequency of spontaneous glutamate-mediated excitatory postsynaptic currents (sEPSCs) in a human subject.

This invention also provides a use of laquinimod in the manufacture of a medicament for increasing the duration or frequency of $GABA_A$-mediated inhibitory postsynaptic currents (sIPSCs) in a human subject.

This invention also provides a use of laquinimod in the manufacture of a medicament for preventing the alteration of $GABA_A$-mediated inhibitory postsynaptic currents (sIPSCs) in a human subject.

This invention also provides a pharmaceutical composition comprising an amount of laquinimod effective for use in treating a human subject suffering from a GABA related disorder.

This invention also provides a pharmaceutical composition comprising an amount of laquinimod effective for use in decreasing the duration or frequency of spontaneous glutamate-mediated excitatory postsynaptic currents (sEPSCs) in a human subject.

This invention also provides a pharmaceutical composition comprising an amount of laquinimod effective for use in increasing the duration or frequency of $GABA_A$-mediated inhibitory postsynaptic currents (sIPSCs) in a human subject.

This invention also provides a pharmaceutical composition comprising an amount of laquinimod effective for use in preventing the alteration of $GABA_A$-mediated inhibitory postsynaptic currents (sIPSCs) in a human subject.

For the foregoing embodiments, each embodiment disclosed herein is contemplated as being applicable to each of the other disclosed embodiment.

Terms

As used herein, and unless stated otherwise, each of the following terms shall have the definition set forth below.

As used herein, "laquinimod" means laquinimod acid or a pharmaceutically acceptable salt thereof.

As used herein, "administering to the subject" means the giving of, dispensing of, or application of medicines, drugs, or remedies to a subject to relieve or cure a pathological condition. Oral administration is one way of administering the instant compounds to the subject.

As used herein, a "GABA related disorder" is a disorder in which a patient suffering from the disorder has defective GABAeric function or low GABA levels. Such diseases include, but are not limited to, schizophrenia, bipolar disorder, epilepsy (seizures), spasticity, stiff-person syndrome (SPS), premenstrual dysphoric disorder, drug addiction, anxiety disorders, fertility disorders, insomnia, spinocerebellar degeneration, neuro-Behçet's syndrome, Parkinson's disease, depression, mania, panic disorder, bi-polar disorder, Alzheimer's disease, Huntington's disease.

As used herein, an "amount" or "dose" of laquinimod as measured in milligrams refers to the milligrams of laquinimod acid present in a preparation, regardless of the form of the preparation. For example, 0.6 mg of laquinimod means the amount of laquinimod acid in a preparation is 0.6 mg, regardless of the form of the preparation. Thus, when in the form of a salt, e.g. a laquinimod sodium salt, the weight of the salt form necessary to provide a dose of 0.6 mg laquinimod would be greater than 0.6 mg due to the presence of the additional salt ion, but would be a molar equivalent amount.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a symptom of a disorder or disease without causing undue adverse side effects. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

A "salt" is salt of the instant compounds which have been modified by making acid or base salts of the compounds. The term "pharmaceutically acceptable salt" in this respect, refers to the relatively non-toxic, inorganic and organic acid or base addition salts of compounds of the present invention.

A pharmaceutically acceptable salt of laquinimod can be used. A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005-0192315 and PCT International Application Publication No. WO 2005/074899, which are hereby incorporated by reference into this application.

As used herein, to "treat" or "treating" encompasses, e.g., inducing inhibition, regression, or stasis of the disorder and/or disease. As used herein, "inhibition" of disease progression or disease complication in a subject means preventing or reducing the disease progression and/or disease complication in the subject.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

A dosage unit as used herein may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit can be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO/2007/146248, each of which is hereby incorporated by reference into this application.

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

It is understood that where a parameter range is provided, all integers within that range, and hundredth thereof, are also provided by the invention. For example, "0.25-2.0 mg/day" includes 0.25 mg/day, 0.26 mg/day, 0.27 mg/day, etc. up to 2.0 mg/day. This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Introduction

By means of neurophysiological recordings from single neurons, we have recently found that, in mice with experimental autoimmune encephalomyelitis (EAE), central neurons develop complex and dynamic alterations of both glutamate- and GABA-mediated transmission, starting in the presymptomatic phase of the disease and evolving independently of demyelination or axonal injury, but in response to specific pro-inflammatory cytokines released by infiltrating T cells and activated microglia. Thus, treatments able to prevent these synaptic alterations are likely to exert clear neuroprotective effects significant for disease progression.

Here, we explored the effects of laquinimod (LQ) on the clinical and synaptic abnormalities of EAE mice, to provide a possible correlate of the neuroprotective action of this drug. We also studied the effect of LQ on basal synaptic transmission to understand whether or not the putative neuroprotective effect of LQ stems from its ability to regulate synaptic transmission, through the modulation of neuronal excitability and limitation of excitotoxic damage.

Materials and Methods

EAE Induction and Disease Evaluation

Female C57BL/6 mice at 6-8 weeks of age were purchased from Charles River (Calco, Milan, Italy) and housed in pathogen-free conditions. All procedures involving animals were performed according to the guidelines of the San Raffaele Scientific Institute Institutional Animal Care and Use Committee.

EAE was induced by immunization with 3 subcutaneous injection of 100 µl each, containing a total of 200 µg of myelin oligodendrocyte glycoprotein (MOG) peptide 35-55 (Multiple Peptide System) in incomplete Freund's adjuvant and 8 mg/ml of *Mycobacterium tuberculosis* (strain H37Ra; Difco). Pertussis toxin (Sigma) (500 ng) was injected on the day of the immunization and again two days later. Body weight and clinical score (0=healthy; 1=limp tail; 2=ataxia and/or paresis of hindlimbs; 3=paralysis of hindlimbs and/or paresis of forelimbs; 4=tetraparalysis; 5=moribund or death) were recorded daily.

EAE mice were treated once daily by subcutaneous (s.c.) injection of LQ (supplied by Teva Pharmaceutical Industries, Netanya, Israel) (thereafter referred as LQ-EAE). LQ was administered at different doses (from 1 to 25 mg/kg) starting the same day of immunization up to 26 days post immunization (d.p.i.). Sham treated EAE mice (thereafter referred as untreated-EAE) and healthy control mice (thereafter referred as HC) were used as controls. Statistical analysis was performed using the unpaired Student's t-test. The significant level was set at $p<0.05$.

Histological Evaluation

At least 5 mice per group were transcardially perfused through the left cardiac ventricle with saline, plus EDTA 0.5 M for 5-10 min followed by fixation with cold 4% paraformaldehyde (PFA) (Sigma, St Louis, Mo.) in 0.1 M phosphate buffer (pH 7.4). Subsequently, spinal cords and brains were carefully dissected out and post-fixed in 4% PFA for 3-4 h and processed for paraffin embedding.

The quantification of neurological damage was performed on 5 µm paraffin CNS sections obtained from HC, LQ-EAE mice, and untreated-EAE mice. Three different staining were used to detect inflammatory infiltrates (H&E), demyelination (Luxol fast blue) and axonal damage (Bielshowsky). Immunohistochemistry for CD3 (pan-T cell marker, Serotec Ltd, Oxford, UK), and BS-I isolectin B4 (biotinilated from Sigma, St Louis, Mo.) was performed to investigate T cells and macrophages within the inflammatory cellular infiltrates, respectively. Antibodies were revealed with appropriate biotin-labeled secondary antibodies (Amersham, UK) and developed with the ABC kit (Vector Laboratories, CA) followed by liquid DAB Substrate Chromogen System (DAKO, CA).

Neuropathological findings were quantified on an average of 18-20 complete cross-sections of spinal cord per mouse taken at 8 different levels of the spinal cord. The number of perivascular inflammatory infiltrates were calculated and expressed as the numbers of inflammatory infiltrates per mm$^2$, demyelinated areas and axonal loss were expressed as percentage of damaged area per mm2. The number of T cells and macrophages lining within the subarachnoid space or infiltrating the CNS parenchyma was calculated and expressed as the number of cells per mm2. An Olympus microscope for the acquisitions of pictures was used.

Statistical analysis was performed using the unpaired Student's t-test. The significant level was set at $p<0.05$.

Electrophysiology

Whole-cell path clamp electrophysiological recordings from single striatal neurons were performed on LQ-EAE mice (treated with 25 mg/kg of LQ), untreated-EAE and HC. Recordings were performed between 25 and 35 dpi. Mice were killed by cervical dislocation under halothane anaesthesia, and corticostriatal coronal slices (200 μm) were prepared from fresh tissue blocks of the brain with the use of a vibratome (Centonze et al., 2007, 2009; Rossi et al., 2010a,b). A single slice was then transferred to a recording chamber and submerged in a continuously flowing artificial CSF (ACSF) (34° C., 2-3 ml/min) gassed with 95% O2-5% CO2. The composition of the control ACSF was (in mM): 126 NaCl, 2.5 KCl, 1.2 MgCl2, 1.2 NaH2PO4, 2.4 CaCl2, 11 Glucose, 25 NaHCO3. Recording pipettes were advanced towards individual striatal cells in the slice under positive pressure and visual control (WinVision 2000, Delta Sistemi, Italy) and, on contact, tight GΩ seals were made by applying negative pressure. The membrane patch was then ruptured by suction and membrane current and potential monitored using an Axopatch 1D patch clamp amplifier (Axon Instruments, Foster City, Calif., USA). Whole-cell access resistances measured in voltage clamp were in the range of 5-20 MΩ. Whole-cell patch clamp recordings were made with borosilicate glass pipettes (1.8 mm o.d.; 2-3 MΩ), in voltage-clamp mode, at the holding potential (HP) of −80 mV. To study spontaneous glutamate-mediated excitatory postsynaptic currents (sEPSCs), the recording pipettes were filled with internal solution of the following composition (mM): K+-gluconate (125), NaCl (10), CaCl2, (1.0), MgCl2 (2.0), 1,2-bis(2-aminophenoxy) ethane-N,N,N,N-tetraacetic acid (BAPTA; 0.5), N-(2-hydroxyethyl)-piperazine-N-sethanesulfonic acid (HEPES; 19), guanosine triphosphate (GTP; 0.3), Mg-adenosine triphosphate (Mg-ATP; 1.0), adjusted to pH 7.3 with KOH. Bicuculline (10 μM) was added to the perfusing solution to block GABA$_A$-mediated transmission. Conversely, to detect spontaneous GABA$_A$mediated inhibitory postsynaptic currents (sIPSCs), intraelectrode solution had the following composition (mM): CsCl (110), K+-gluconate (30), ethylene glycolbis(β-aminoethyl ether)-N,N,N',N'-tetra-acetic acid (EGTA; 1.1), HEPES (10), CaCl2 (0.1), Mg-ATP (4), Na-GTP (0.3). MK-801 (30 μM) and CNQX (10 μM) were added to the external solution to block, respectively, NMDA and non-NMDA glutamate receptors. Synaptic events were stored by using P-CLAMP (Axon Instruments) and analyzed off line on a personal computer with Mini Analysis 5.1 (Synaptosoft, Leonia, N.J., USA) software. The detection threshold of spontaneous IPSCs and EPSCs was set at twice the baseline noise. The fact that no false events would be identified was confirmed by visual inspection for each experiment. Offline analysis was performed on spontaneous and miniature synaptic events recorded during fixed time epochs (3-5 min, 3-6 samplings), sampled every 5 or 10 minutes. Only cells that exhibited stable frequencies in control (less than 20% changes during the control samplings) were taken into account. For kinetic analysis, events with peak amplitude between 10 and 50 pA were grouped, aligned by half-rise time, normalized by peak amplitude. In each cell, the events were averaged to obtain rise times, decay times, and half widths (Centonze et al., 2009; Rossi et al., 2010a,b).

Drugs were applied by dissolving them to the desired final concentration in the bathing ACSF. Drugs were: CNQX (10 μM), HU210 (1 μM), MK-801 (30 μM), HU210 (1 μM) (from Tocris Cookson, Bristol, UK), bicuculline (10 μM) (from Sigma-RBI, St. Louis, USA). LQ (0.3, 1, 10, 30 μM).

For data presented as mean±SE, n indicates the number of cells. One to six cells per animal were recorded. For each type of experiment and time point, at least four distinct animals were employed from each experimental group. Multiple comparisons were analysed by one-way ANOVA followed by Tukey's HSD test. Comparisons between two groups were analysed by paired or unpaired Student's t-test. The significant level was set at $p<0.05$.

EXAMPLE 1

Effect of LQ Treatment in EAE Mice

As previously demonstrated, we confirmed that preventive treatment (0-26 d.p.i.) with daily s.c. administration of LQ was able to ameliorate EAE in a dose dependent manner (FIG. 1). All 15 untreated-EAE mice developed the disease, 13/15 (86.6%) of 1 mg/kg LQ-EAE mice, 12/15 (80%) of 5 mg/kg LQ-EAE mice, and 6/15 (40%) of 25 mg/kg LQ-EAE mice. Onset was also progressively delayed depending of the dose of LQ; the untreated-EAE group had a mean disease onset at 11.9 (±2.33), the 1 mg/kg LQ-EAE mice had a mean disease onset at 11.9 (±2.47), the 5 mg/kg LQ-EAE mice had a mean disease onset at 14.6 (±4.29), and, the mg/kg LQ-EAE mice had a mean disease onset at 13.5 (±2.43). Maximum disease score was 3.5 in sham treated and in 1 mg/kg LQ-EAE mice while it was 3 in 5 mg/kg LQ-EAE mice and 1.5 in 25 mg/kg LQ-EAE mice. Cumulative score (0-26 dpi) was 27.5 in untreated EAE mice and 27.3 in 1 mg/kg LQ-EAE mice, 21.5 in 5 mg/kg LQ-EAE mice, and 21.3 in 25 mg/kg LQ-EAE mice.

Pathological examination of spinal cords confirmed clinical readouts by showing a reduction in numbers of infiltrates within the spinal cord sections (FIG. 2). Cellular infiltrates in LQ-EAE mice displayed a changed composition with a diminished number of T lymphocytes (CD3+) and microglia/macrophages (Isolectin B4+) (FIG. 2). Demyelination and axonal loss were also reduced in LQ-EAE mice compared to control, again in a dose dependent manner (FIG. 2).

EXAMPLE 2

Effect of LQ on Glutamate Transmission in EAE

As previously demonstrated (Centonze et al., 2009), the duration of glutamate-mediated sEPSCs was increased in striatal neurons of untreated-EAE mice. A slower decay time accounted for increased sEPSC duration (decay time: untreated-EAE 5.4±0.4 ms, HC 3.4±0.2 ms; half-width: untreated-EAE 6.4±0.4 ms, HC 4.0±0.3 ms; n=18 for both groups, p<0.01). LQ treatment failed to prevent the alteration of sEPSC shape but significantly reduced it (LQ-EAE: decay time 4.2±0.3 ms, half-width 5.0±0.3 ms, n=20; p<0.05 respect to untreated-EAE, p<0.05 respect to HC) (FIG. 3A). Neither EAE induction nor LQ treatment affected rise time and amplitude of sEPSCs (rise time: untreated-EAE 1.05±0.1 ms, LQ-EAE 0.98±0.1 ms, HC 1.03±0.1 ms; amplitude: untreated-EAE 11.1±0.8 pA, LQ-EAE 12.2±1.1 pA, HC 12.0±1.0 pA; n=at least 18, p>0.05) (FIG. 3A,B,D).

Not only the duration, but also the frequency of sEPSCs is increased in EAE mice (Centonze et al., 2009; Rossi et al., 2010a), as expected for both pre- and postsynaptic abnormalities of glutamatergic transmission (untreated-EAE mice 4.0±0.2 Hz, HC 2.7±0.2 Hz n=at least 18 for both groups, p<0.01). In accordance with the data on the kinetic properties of sEPSCs, the frequency of sEPSCs was reduced but not normalized by LQ treatment (LQ-EAE 3.4±0.4 Hz; n=20, p>0.05 respect to both EAE-untreated and HC) (FIG. 3C,D).

EXAMPLE 3

Effect of LQ on GABA Transmission in EAE

Figure 4:
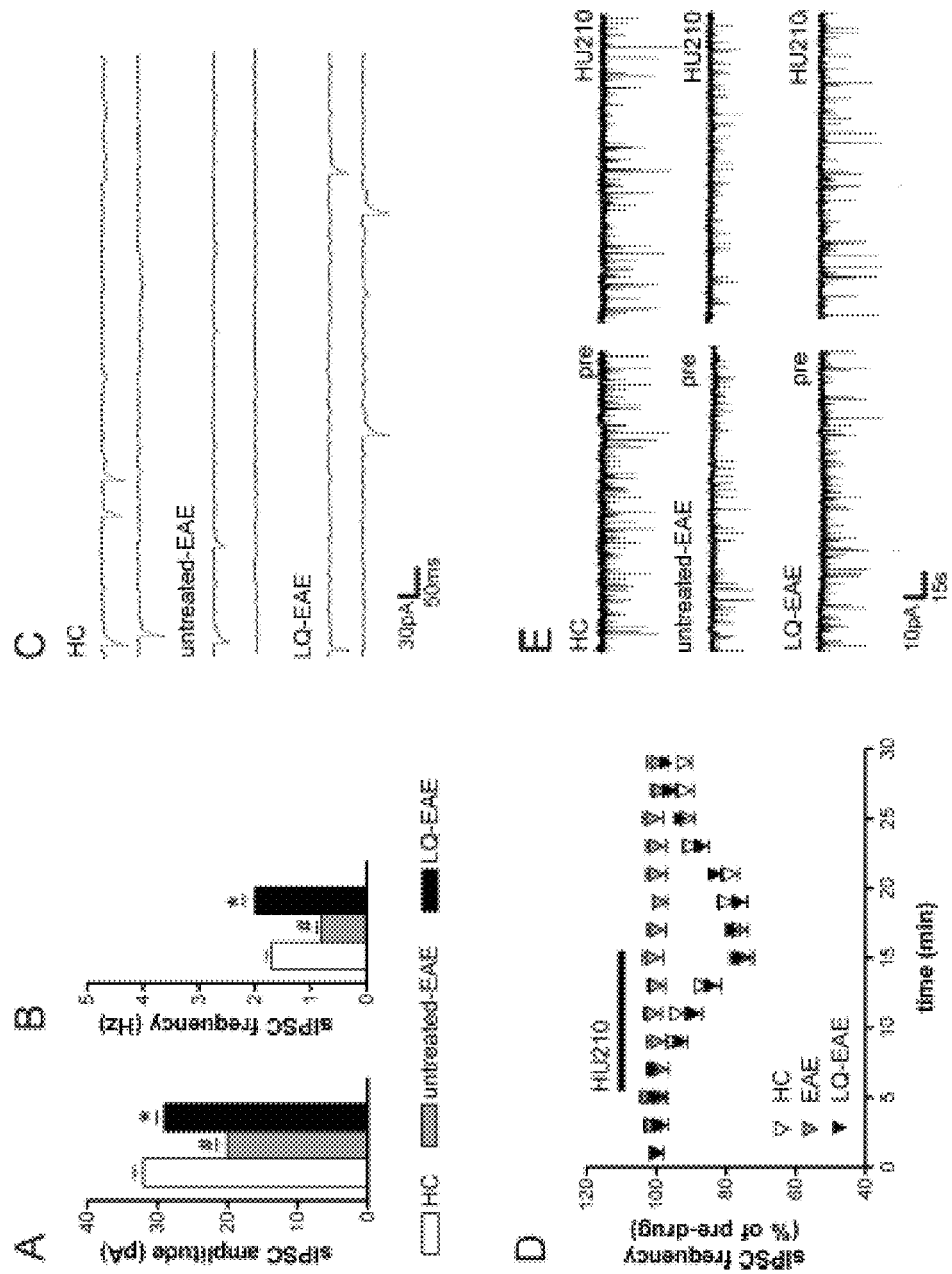
FIG. 4: Effect of prophylactic LQ treatment (25 mg/kg) on EAE-induced synaptic alterations of striatal GABAergic transmission. (A, B) EAE induction markedly affects GABA transmission, inhibiting both amplitude (A) and frequency (B) of sIPSCs. LQ treatment fully prevented the alterations of sIPSCs. (C) The electrophysiological traces are examples of sIPSCs recorded from striatal neurons of HC, untreated-EAE and LQ-EAE mice. (D) The graph shows that LQ treatment completely restored the effect of CB1 receptor agonist HU210 on sIPSCs. (E) The electrophysiological traces are examples of sIPSCs recorded from striatal neurons of HC, untreated-EAE and LQ-EAE mice before and during HU210 application. Statistical analysis was performed using ANOVA followed by Tukey HSD Test. *$p<0.05$ compared to untreated-EAE group; # means $p<0.05$ compared to HC.

Alterations of synaptic inhibition occur in parallel with abnormal glutamate transmission in EAE (Rossi et al., 2010b). According to previous report, both frequency and amplitude of sIPSCs were markedly inhibited by EAE induction (frequency: untreated-EAE 0.8±0.1 Hz, HC 1.7±0.1 ms; amplitude: untreated-EAE 20±1.5 pA, HC 32±1.3 pA; n=20 for both groups, p<0.01). LQ treatment fully prevented the alterations of sIPSCs (LQ-EAE: frequency 2.0±0.2 Hz, amplitude 29±1.1 pA; n=20, p<0.05 respect to untreated-EAE, p>0.05 respect to HC) (FIG. 4A-C). Furthermore, we also investigated the sensitivity of GABA synapses to the stimulation of cannabinoid receptor (CB)1, since we have previously demonstrated the loss of CB1-mediated control of GABA transmission in EAE mice (Centonze et al., 2007). Application of the cannabinoid CB1 receptor agonist HU210 (10 min, n=8) significantly reduced sIPSCs frequency in control slices (76±3% respect to pre-drug values, p<0.05). In striatal neurons from untreated EAE mice, the effects of HU210 were completely abolished (n=10, 101±3% respect to pre-drug values, p>0.05). Of note, in LQ-EAE mice the effects of HU210 were normal (n=10, 75±3% respect to pre-drug values, p<0.05), indicating the beneficial effects of LQ administration were associated with preserved cannabinoid CB1 receptor sensitivity at striatal GABAergic synapses (FIG. 4D,E).

EXAMPLE 4

Effect of LQ on Basal Synaptic Transmission

The data above indicate that LQ directly alters sEPSCs and sIPSCs in EAE mice because it modulates basal glutamate and GABA transmission at central synapses. Nevertheless, an indirect immunomodulatory mechanism has to be excluded to evaluate a direct effect of the drug on neuronal functionality. Thus, we tested the effect of LQ, applied in the bathing solutions of corticostriatal slices of wild type mice, on spontaneous synaptic transmission.

In EAE mice, the CNS concentration of LQ administered systemically has been reported to be as high as 13% of exposure in peripheral blood (Bruck et al, 2011). Thus, the s.c. administration of 25 mg/kg of LQ should equal a CNS concentration of 0.3-1 µM. Thus, to mimic the in vivo situation, 1 µM of LQ was applied on brain slices for 12 minutes. This failed to alter frequency (FIG. 5A,C), amplitude (FIG. 5B,D) and kinetic properties (sIPSC rise time: 101±2%, sIPSC decay time: 98±3%; sEPSC rise time: 99±1%, sEPSC decay time: 101±2%, not shown) of both sEPSCs and sIPSCs recorded from control neurons (n=at least 10 neurons for each parameters, p>0.05 for each parameters compared to pre-drug values), indicating that LQ is able to prevent the synaptic alterations induced by EAE, without interfering with basal synaptic transmission.

Surprisingly, at higher concentrations, LQ showed direct effects on neuronal synaptic activity, by enhancing inhibitory transmission and reducing excitatory transmission. Bath application of LQ (10-30 µM) significantly increased sIPSC frequency (p<0.01) but not amplitude (p>0.05 for each parameters) in all the tested control neurons (n=8 for both concentrations) (FIG. 5A,B), indicating a presynaptic effect of this drug on modulating GABAergic transmission. Dose-response curve is reported in FIG. 5C.

Figure 5:
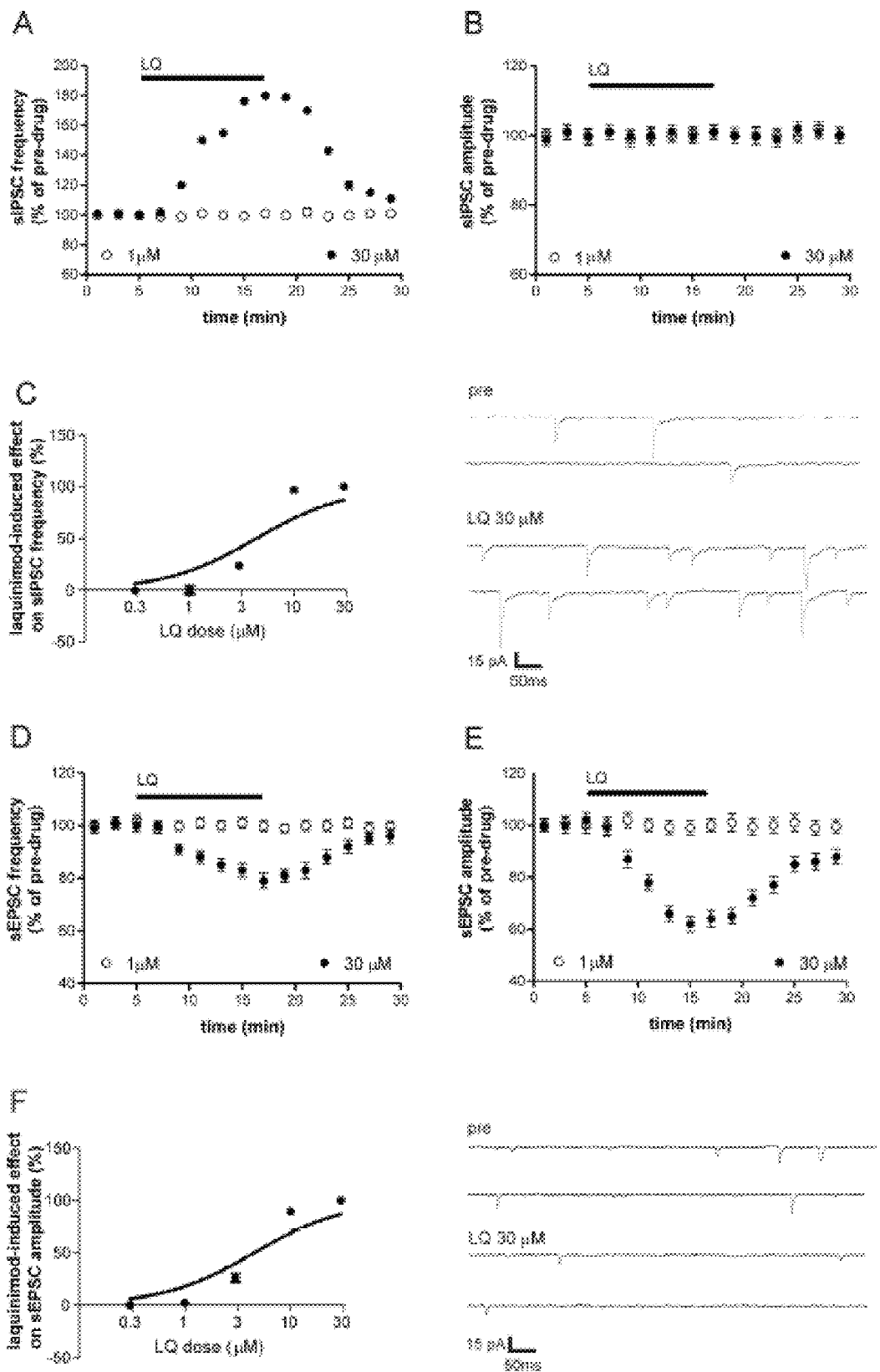
FIG. 5: Effect of LQ on basal synaptic transmission. (A, B) The graphs show the effect of bath application of LQ on GABAergic transmission. LQ 1 μM failed to alter the frequency (A) and the amplitude (B) of sIPSCs recorded from control neurons. Conversely at higher concentration, LQ was able to increase the frequency of sIPSCs. (C) The graph shows the dose-response curve of the LQ-induced increase of sIPSC frequency. EC50=4.3 μM. The traces on the right are examples of voltage clamp recordings before and during the application of LQ 30 μM in control neurons. (D, E) The graphs show the effect of bath application of LQ on glutamatergic transmission. LQ 1 μM failed to alter the frequency (D) and the amplitude (E) of sEPSCs recorded from control neurons. Conversely at higher concentration, LQ induced a significant reduction of both parameters. F. The graph shows the dose-response curve of the LQ-induced decrease of sEPSC amplitude. EC50=4.5 μM. The traces on the right are examples of voltage clamp recordings before and during the application of LQ 30 μM in control neurons.

Pharmacological blockade of $GABA_A$ receptors with bicuculline fully blocked sIPSCs recorded in the presence of LQ (n=5, not shown), such as in control conditions (n=3, not shown). Moreover bath application of LQ (10-30 µM) revealed a significant postsynaptic effect on excitatory synaptic transmission by reducing sEPSC amplitude in all the tested control neurons (n=10 for both concentrations, p<0.01). A significant reduction of the frequency of sEPSCs was also recorded in the presence of the highest concentration of LQ (n=7, 83±2.7% respect to pre-drug values, p<0.05) (FIG. 5D,E). Dose-response curve is reported in FIG. 5F. Pharmacological blockade of AMPA receptors with CNQX fully blocked sEPSCs recorded in the presence of LQ (n=5, not shown), such as in control conditions (n=4, not shown).

Discussion

It has been variably recognized that early axonal damage is one of the most important neuropathological features of MS (Trapp et al., 1998. Several human and experimental evidence support this hypothesis. Early phases of MS are characterized by focal cortical thinning and thalamic neurodegeneration (Chard et al., 2002) and spinal cord atrophy was already found in patients with clinically isolated syndrome (Brex P E et al., 2001). In EAE mice, synaptic derangement occurs, even before disease onset, as a consequence of the massive release of primary inflammatory cytokines (Centonze et al., 2009). Th17 cells from EAE mice may directly damage axons via a mechanism possibly involving IL-17 release (Siffrin et al., 2010). Extensive alterations of intra-axonal mitochondria preceding axonal morphology changes occur in early phase of EAE possibly via a contributing role of reactive oxygen and nitrogen species (ROS/RNS) (Nikic et al., 2011).

The present study demonstrates that the clinical, synaptic and neuropathological defects of EAE mice can be significantly attenuated by LQ, suggesting that treatment with this pharmacological agent could afford neuroprotective effects. We have shown, in fact, that the immunomodulatory drug LQ when therapeutically administered to EAE mice was able to reduce glutamatergic while increasing GABAergic synaptic currents in the striatum. As a consequence, glutamatergic excitotoxicity is limited and axonal damage significantly reduced in LQ-treated compared to untreated EAE mice. If LQ modulates synaptic transmission directly or indirectly, via the release of third party molecule(s), is not known so far but the electrophysiological evidence we collected indicate that LQ is capable of inducing a cascade of events leading to the blockage of glutamatergic current and to the increase GABAergic currents by acting at both pre- and postsynaptic level. The sensitivity of the cannabinoid receptor (CB)1 on GABAergic synapses was also preserved by LQ treatment. It is of note that endocannabinoids, which are molecules known to ameliorate EAE and provide some therapeutic benefit to MS patients (Baker et al., 2007), are able to reduce glutamatergic currents via increasing intracellular calcium at pre and post synaptic level via CB1 receptor triggering (Centonze et al., 2007).

There is evidence indicating an immunomodulatory role of LQ in EAE and MS patients. LQ was shown to be able to interfere with the inflammatory phase of EAE by inducing a Th1-Th2 shift (Yang et al. 2004), suppressing genes related to antigen presentation (Gurevich M et al 2010), and affecting antigen presentation capacity of dendritic cells (DC) (Schulze-Topphoff U et al. 2012). Thus, the immunomodulatory mode of action can be primarily advocated to partially explain the neuroprotective effect of LQ in EAE. However, LQ is able to cross the blood brain barrier when systemically administered (Brück et al., 2011) so it can reach the CNS and exert in situ a direct neuroprotective effect. In agreement with that mode of action, when we tested on acute brain slices whether LQ can directly modulate synaptic activity, we found results that were superimposable to those obtained in vivo. Of note, at lower dose LQ was able to prevent the synaptic alterations induced by EAE, without interfering with physiological synaptic transmission, suggesting a direct neuroprotective activity. At higher concentrations, LQ had direct effects on both excitatory and inhibitory synaptic activity. Further studies are needed to validate these results.

We cannot exclude that part of the neuropotective effect observed in vivo in both patients with MS and EAE rodents can be attributed to the capacity of LQ to significantly and persistently increase circulating BDNF levels (Thöne et al. 2012). Nevertheless, our data might, at least in part, explain some of the in vivo evidence obtained in patients with MS and in mice with EAE and, in particular the demonstration that LQ is able to interfere with established chronic-relapsing EAE (Brunmark et al. 2002, Wegner C. et al., 2010), and to reduce the occurrence of "black holes" in humans (Comi et al. 2008). Even more importantly, our data might also support data from phase III trials demonstrating that LQ not only reduced the relapse rate but also slowed the progression of disability in patients with RR-MS (Comi et al., 2012). In conclusion, our data support the concept that LQ might act as neuroprotective drug since it is able to limit axonal damage via the modulation of neuronal excitability and the limitation of excitotoxic damage induced by the alteration of the synaptic transmission.

The ability of laquinimod to modulate CB1 and GABA function suggests that laquinimod may be useful to treat CB1 receptor and GABA related disorders.

EXAMPLE 5

Rat Model of Schizophrenia

Laquinimod is tested in a rat model of schizophrenia. Rats receiving an amount of laquinimod demonstrate positive results compared to control rats.

EXAMPLE 6

Human Schizophrenia Trial

Laquinimod is administered to human subjects diagnosed with schizophrenia. Human subjects receiving an amount of laquinimod demonstrate positive results compared to the control group. Specifically, human subjects experienced an alleviation of delusions, hallucinations, disorganized symptom cluster, blunted affect, poverty of speech, anhedonia or asociality.

EXAMPLE 7

Rat Model of Epilepsy

Laquinimod is tested in a rat model of epilepsy. Rats receiving an amount of laquinimod demonstrate positive results compared to control rats.

EXAMPLE 8

Human Epilepsy Trial

Laquinimod is administered to human subjects diagnosed with epilepsy. Human subjects receiving an amount of laquinimod demonstrate positive results compared to the control group. Specifically, human subjects experienced a an alleviation in auras, simple partial seizures, complex partial seizures, generalized seizures, infantile spasms, absence seizures, generalized tonic-clonic seizures, atonic seizures, myoclonic seizures, febrile seizures, status epilepticus or epilepsia partialis continua.

EXAMPLE 9

Rat Model of Spasticity

Laquinimod is tested in a rat model of spasticity. Rats receiving an amount of laquinimod demonstrate positive results compared to control rats.

EXAMPLE 10

Human Spasticity Trial

Laquinimod is administered to human subjects diagnosed with spasticity. Human subjects receiving an amount of laquinimod demonstrate positive results compared to the control group. Specifically, human subjects experienced an alleviation in spasticity, hemiplegia, paraplegia, quadriplegia, or diplegia.

EXAMPLE 11

Mouse Model of ADHD

DAT cocaine-insensitive (DAT-CI) mice have a triple point-mutation in the cocaine-binding site of the dopamine transmitter (DAT) gene. The behavior of DAT-CI mice mimics human ADHD behavior. As previously described, the sensitivity of CB1 receptors controlling GABA-mediated synaptic currents in the striatum of DAT-CI mice was completely lost. (Castelli et al., 2011).

DAT-CI mice receiving laquinimod demonstrate decreased locomotor activity compared to control mice. DAT-CI mice receiving an amount of laquinimod also demonstrate restored sensitivity of CB1 receptors to CB1 receptor agonist HU210.

REFERENCES

Baker D, Jackson S J, Pryce G. Cannabinoid control of neuroinflammation related to multiple sclerosis. Br J. Pharmacol. 2007; 152:649-54.

Bernes F M, Berretta S. GABAergic Interneurons: Implications for understanding schizophrenia and bipolar disorder. Neuropsychopharmacology 2001; 25:1-27.

Brex P A, Leary S M, O'Riordan J I, Miszkiel K A, Plant G T, Thompson A J, Miller D H. Measurement of spinal cord area in clinically isolated syndromes suggestive of multiple sclerosis. J Neurol Neurosurg Psychiatry. 2001; 70:544-7.

Brück W, Wegner C. Insight into the mechanism of laquinimod action. J Neurol Sci. 2011; 306:173-9.

Brunmark C, Runstrom A, Ohlsson L, Sparre B, Brodin T, Aström M, Hedlund G. The new orally active immunoregulator laquinimod (ABR-215062) effectively inhibits development and relapses of experimental autoimmune encephalomyelitis. J. Neuroimmunol. 2002; 130:163-72.

Castelli M, Federici M, Rossi S, De Chiara V, Napolitano F, Studer V, Motta C, Sacchetti L, Romano R, Musella A, Bernardi G, Siracusano A, Gu H, Mercuri N, Usiello A, Centonze D. Loss of striatal cannabinoid CB1 receptor function in attention-deficit/hyperactivity disorder mice with point-mutation of the dopamine transporter. European Journal of Neuroscience 2011; 34:1369-1377.

Centonze D, Bari M, Rossi S, Prosperetti C, Furlan R, Fezza F, De Chiara V, Battistini L, Bernardi G, Bernardini S, Martino G, Maccarrone M The endocannabinoid system is dysregulated in multiple sclerosis and in experimental autoimmune encephalomyelitis. Brain. 2007; 130:2543-53.

Centonze D, Muzio L, Rossi S, Furlan R, Bernardi G, Martino G. The link between inflammation, synaptic transmission and neurodegeneration in multiple sclerosis. Cell Death Differ. 2010; 17:1083-91.

Chard D T, Griffin C M, Parker G J, Kapoor R, Thompson A J, Miller D H. Brain atrophy in clinically early relapsing-remitting multiple sclerosis. Brain. 2002; 125:327-37.

Comi G, Pulizzi A, Rovaris M, Abramsky O, Arbizu T, Boiko A, Gold R, Havrdova E, Komoly S, Selmaj K, Sharrack B, Filippi M; LAQ/5062 Study Group Effect of laquinimod on MRImonitored disease activity in patients with relapsing-remitting multiple sclerosis: a multicentre, randomised, double-blind, placebo-controlled phase IIb study. Lancet. 2008; 371:2085-92.

Comi G, Jeffery D, Kappos L, Montalban X, Boyko A, Rocca M A, Filippi M; ALLEGRO Study Group (2012). Placebo-controlled trial of oral laquinimod for multiple sclerosis. N Engl J. Med. 2012; 366:1000-9.

Gurevich M, Gritzman T, Orbach R, Tuller T, Feldman A, Achiron A Laquinimod suppress antigen presentation in relapsing-remitting multiple sclerosis: in-vitro high-throughput gene expression study. J. Neuroimmunol. 2010; 221:87-94.

Kuroda H, Ogawa N, Yamawaki Y, Nukina I, Ofuji T, Yamamoto M, Otsuki S. Cerebrospinal fluid GABA levels in various neurological and psychiatric diseases. J Neurol Neurosurg Psychiatry 1982; 45:257-260.

Möhler H. $GABA_A$ Receptors in Central Nervous System Disease: Anxiety, Epilepsy, and Insomnia, Journal of Receptors and Signal Transduction 2006; 26, 5-6:731-740.

Nikić I, Merkler D, Sorbara C, Brinkoetter M, Kreutzfeldt M, Bareyre F M, Brück W, Bishop D, Misgeld T, Kerschensteiner M. A reversible form of axon damage in experimental autoimmune encephalomyelitis and multiple sclerosis. Nat. Med. 2011; 17:495-9.

Olesen R W. "GABA". Neuropsychopharmacology: The Fifth Generation of Progress (Davis K, Charney D, Coyle, and Nemeroff C Eds.). American College of Neuropsychopharmacology 2002.

Rossi S, Muzio L, De Chiara V, Grasselli G, Musella A, Musumeci G, Mandolesi G, De Ceglia R, Maida S, Biffi E, Pedrocchi A, Menegon A, Bernardi G, Furlan R, Martino G, Centonze D. Impaired striatal GABA transmission in experimental autoimmune encephalomyelitis. Brain Behav Immun. 2011; 25:947-56.

Rossi S, Bernardi G, Centonze D. The endocannabinoid system in the inflammatory and neurodegenerative processes of multiple sclerosis and of amyotrophic lateral sclerosis. Exp Neurol. 2010a; 224:92-102.

Rossi S, De Chiara V, Furlan R, Musella A, Cavasinni F, Muzio L, Bernardi G, Martino G, Centonze D Abnormal activity of the Na/Ca exchanger enhances glutamate transmission in experimental autoimmune encephalomyelitis. Brain Behav Immun. 2010b; 24:1379-85.

Schulze-Topphoff U, Shetty A, Varrin-Doyer M, Molnarfi N, Sagan S A, Sobel R A, Nelson P A, Zamvil S S. Laquinimod, a Quinoline-3-Carboxamide, Induces Type II Myeloid Cells That Modulate Central Nervous System Autoimmunity. PLoS One. 2012; 7:e33797.

Siffrin V, Radbruch H, Glumm R, Niesner R, Paterka M, Herz J, Leuenberger T, Lehmann S M, Luenstedt S, Rinnenthal J L, Laube G, Luche H, Lehnardt S, Fehling H J, Griesbeck O, Zipp F. In vivo imaging of partially reversible th17 cell-induced neuronal dysfunction in the course of encephalomyelitis. Immunity. 2010; 33:424-36.

Sullivan S D, Moenter S M. Prenatal androgens alter GABAergic drive to gonadotropin-releasing hormone neurons: implications for a common fertility disorder. Proc Natl Acad Sci USA. 2004 May 4; 101(18):7129-34.

Thöne J, Ellrichmann G, Seubert S, Peruga I, Lee D H, Conrad R, Hayardeny L, Comi G, Wiese S, Linker R A, Gold R. Modulation of Autoimmune Demyelination by Laquinimod via Induction of Brain-Derived Neurotrophic Factor. American J Pathol 2012; 180.

Trapp B D, Ransohoff R, Rudick R. Axonal pathology in multiple sclerosis: relationship to neurologic disability. Curr Opin Neurol. 1999; 12:295-302.

Wegner C, Stadelmann C, Pförtner R, Raymond E, Feigelson S, Alon R, Timan B, Hayardeny L, Brück W. Laquinimod interferes with migratory capacity of T cells and reduces IL-17 levels, inflammatory demyelination and acute axonal damage in mice with experimental autoimmune encephalomyelitis. J. Neuroimmunol. 2010; 227:133-43.

Wenk G, Walker L, Price D, Cork L. Loss of NMDA, but not $GABA-A$, binding in the brains of aged rats and monkeys. Neurobiology of Aging 1991; 12:93-98.

Wong C G T, Bottiglieri T, Snead III O C. GABA, γ-Hydroxybutyric Acid, and Neurological Disease. Ann Neurol 2003; 54: (suppl 6)S3-S12.

Yang J S, Xu L Y, Xiao B G, Hedlund G, Link H. Laquinimod (ABR-215062) suppresses the development of experimental autoimmune encephalomyelitis, modulates the Th1/Th2 balance and induces the Th3 cytokine TGF-beta in Lewis rats. J. Neuroimmunol. 2004; 156:3-9.

What is claimed is:

1. A method of treating a subject suffering from a GABA related disorder comprising periodically administering to the subject an effective amount of laquinimod or pharmaceutically acceptable salt thereof in an amount effective to treat the subject, wherein the GABA related disorder is schizophrenia, epilepsy (seizures), spasticity, stiff-person syndrome (SPS), premenstrual dysphoric disorder, drug addiction, insomnia, spinocerebellar degeneration, or neuro-Behcet's syndrome.

2. The method of claim 1, wherein the subject is human.

3. The method of claim 1, wherein the GABA related disorder is schizophrenia, epilepsy (seizures), or spasticity.

4. The method of claim 1, wherein the GABA concentration in the central nervous system of the subject is increased.

5. The method of claim 1, wherein the laquinimod is administered via oral administration.

6. The method of claim 1, wherein the laquinimod is administered daily.

7. The method of claim 1, wherein the laquinimod is administered more often than once daily.

8. The method of claim 1, wherein the laquinimod is administered less often than once daily.

9. The method of claim 1, wherein the amount of laquinimod administered is less than 0.6 mg/day.

10. The method of claim 1, wherein the amount of laquinimod administered is 0.1-40.0 mg/day.

11. The method of claim 10, wherein the amount of laquinimod administered is 0.1-2.5 mg/day.

12. The method of claim 10, wherein the amount of laquinimod administered is 0.25-2.0 mg/day.

13. The method of claim 10, wherein the amount of laquinimod administered is 0.5-1.2 mg/day.

14. The method of claim 10, wherein the amount of laquinimod administered is 0.25 mg/day, 0.3 mg/day, 0.5 mg/day, 0.6 mg/day, 1.0 mg/day, 1.2 mg/day, 1.5 mg/day, or 2.0 mg/day.

15. The method of claim 1, wherein the pharmaceutically acceptable salt of laquinimod is laquinimod sodium.

16. The method of claim 3, wherein the laquinimod is administered via oral administration.

17. The method of claim 16, wherein the amount of laquinimod administered is 0.1-40.0 mg/day.

18. The method of claim 17, wherein the amount of laquinimod administered is 0.25-2.0 mg/day.

19. The method of claim 17, wherein the amount of laquinimod administered is 0.25 mg/day, 0.3 mg/day, 0.5 mg/day, 0.6 mg/day, 1.0 mg/day, 1.2 mg/day, 1.5 mg/day, or 2.0 mg/day.

20. The method of claim 19, wherein the pharmaceutically acceptable salt of laquinimod is laquinimod sodium.

\* \* \* \* \*